United States Patent
Shannon

[11] Patent Number: 6,165,570
[45] Date of Patent: Dec. 26, 2000

[54] DEER ATTRACTANT

[76] Inventor: L. Keith Shannon, 9405 Sand Valley Rd., Avera, Ga. 30803

[21] Appl. No.: 09/293,818

[22] Filed: Apr. 16, 1999

Related U.S. Application Data

[60] Provisional application No. 60/084,692, May 8, 1998.

[51] Int. Cl.⁷ ....................................................... B32B 1/06

[52] U.S. Cl. ........................... 428/34.1; 428/99; 428/100; 424/84

[58] Field of Search ............................ 428/34.1, 99, 100; 424/84

[56] References Cited

U.S. PATENT DOCUMENTS 4,944,940   7/1990   Christenson, II ........................ 424/84

*Primary Examiner*—Alexander S. Thomas
*Attorney, Agent, or Firm*—Michael A Mann; Michael E Wever; Nexsen Pruet Jacobs & Pollard LLP

[57] ABSTRACT

A deer attractant comprising an air-permeable container holding hair taken from the tarsal gland region of a deer. Instead of using deer tissue or urine that may spoil relatively quickly, only the hair from the tarsal gland region are collected. The collected hair is placed in an air-permeable container. In use, the container is preferably hung on a tree or other elevated structure to maximize the emanation of the odor to attract deer or from a slowly moving vehicle to create a scent trail.

20 Claims, 1 Drawing Sheet

DEER ATTRACTANT

This application claims the benefit of U.S. Provisional Application No. 60/084,692, filed May 8, 1998 (May 8, 1998).

BACKGROUND OF THE INVENTION

1. Field of the Invention

The present invention relates to an article for attracting deer, and, in particular, deer hair in an air permeable container.

2. Discussion of Background

Deer rely on their sense of smell for information about their surrounding environment. Depending upon the particular scent they detect, deer may respond by indifference, fear or attraction. The scent of a female deer, for example, will attract a male deer. A hunter, wildlife enthusiast, or photographer may try to duplicate a particular attractive scent to attract deer.

One method in which deer communicate is by using the scent of volatile compounds secreted by their tarsal glands. The tarsal gland is located on the inside hind legs of deer as illustrated in FIGS. 2–3. The tarsal gland is a source of identification with each deer having its own unique smell. To utilize the tarsal glands, a deer will rub its two tarsal glands together while urinating over them. This urine contains an odor that identifies certain characteristics of the deer such as gender, social status, and physical condition. The tarsal gland tissue (sebaceous gland) secret sebum that adheres to the tarsal hair which selects certain fat soluble compounds from the urine, which gives the tarsal hair its individually pungent smell. Deer are naturally curious about the smell of a new deer in their area.

During mating season or rut, bucks use the secretions from their tarsal glands to mark their territory and attract does. A buck will mark off his breeding territory by creating several mating scrapes. A scrape is a circular area that has been cleared of leaves or other debris. Upon clearing the area, the buck will mark the scrape by urinating over his tarsal glands. These scrapes will be worked on a regular basis. This serves to announce and maintain the buck's presence and dominance to the does and other bucks in the area. Does may be attracted to the area of a dominant buck during estrus, while less dominant bucks generally avoid confrontation with the dominant buck. The presence of another buck's scent on scrapes of a dominant buck, presents a direct challenge to the dominant buck.

Various products have been devised to duplicate these natural odors that attract deer. Numerous patents on deer attractants have been issued on fluids, such as deer urine, that are sprayed or dispensed. U.S. Pat. No. 4,944,940 issued to Christenson, II, combines the use of deer urine with the tarsal gland. In this patent, the tarsal gland is dried, either naturally, by convection heating or by freeze-drying, until use. The gland is rehydrated to activate it by adding a quantity of urine at the hunting site. Unfortunately, tarsal gland tissue has a limited shelf life. If the gland is not preserved, the tissue becomes "spoiled" very quickly thereby making it unattractive to deer and impossible to market. Moreover, preservation methods, such as freeze-drying, tend to alter and destroy the volatile compounds carried by the tarsal hair so that the rehydrated odor does not have its intended attractive effect. Therefore, there is a need for a deer attractant that contains all of the naturally occurring volatile compounds and has a long shelf life.

SUMMARY OF THE INVENTION

According to its major aspects and broadly stated, the present invention is an article for attracting deer and a process for making a deer attractant. In particular, the present invention relates to an air permeable container holding hair taken from the tarsal gland region of a deer. Instead of using deer tissue or urine that may spoil relatively quickly, only the hair from the tarsal gland is collected. The collected hair is placed in an air-permeable container. In use, the container is preferably hung from a tree or other elevated structure to maximize the diffusion of the odor to the surroundings in order to attract deer.

A major advantage of the present invention is that by eliminating the tarsal gland and other cutaneous tissue and providing only hair with its naturally occurring volatile compounds, the scent and smell of a deer as it occurs on a real deer is provided without alteration.

Another important advantage of the present invention is the ability to use the product repeatedly without degradation or contamination. Fresh tarsal gland tissues begins to "spoil" immediately, and freeze dried tarsal glad to which urine has been added does not duplicate the naturally occurring volatiles on unaltered hair. The present invention, on the other hand, does not rely on freeze drying or the application of deer urine but can be used multiple times without spoiling or losing its all of its naturally occurring volatile compounds and deer-attracting qualities.

The use of hair from the tarsal gland region without actually using tarsal gland tissue is a major feature of the present invention. Although the hair contains the volatile compounds that attract deer, eliminating the need for the tarsal gland itself reduces many contamination and handling concerns.

A major advantage of the present invention is the extended life of the attractant. Since items that easily "spoil" such as tarsal gland tissue and urine are not used, the life of the product is greatly increased. Consequently, preservation techniques that degrade and destroy the natural volatiles, such as freeze-drying, are unnecessary. As a result, the present invention is a much more effective, durable deer attractant.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
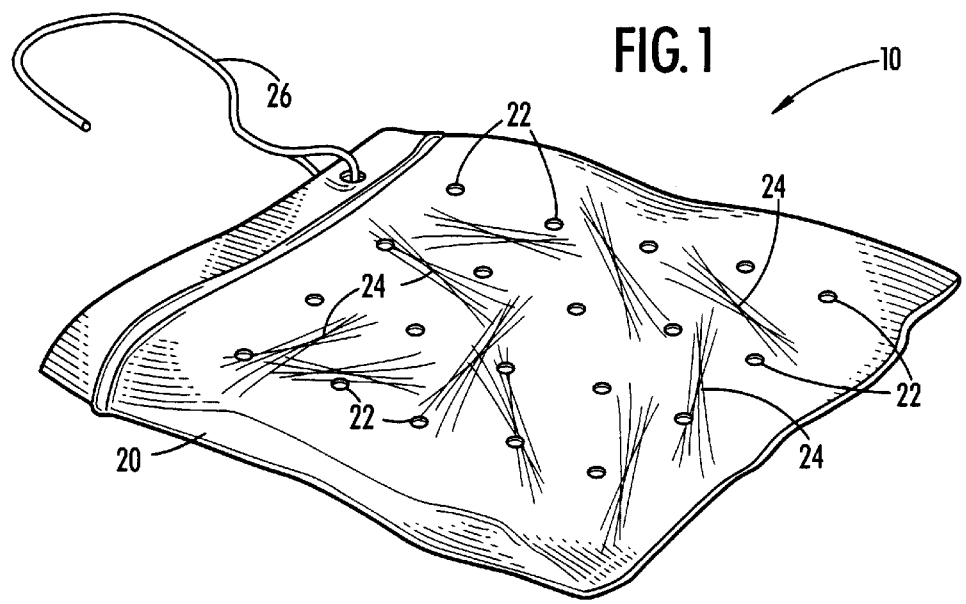
FIG. 1 is a perspective view of a deer attractant, according to a preferred embodiment of the present invention.
Figure 2:
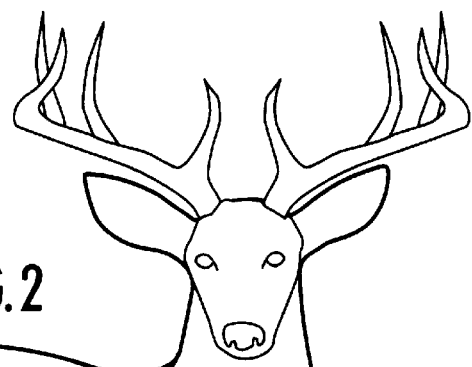
FIG. 2 is a perspective view of a buck with the tarsal gland region shown in dashed lines.
Figure 3:
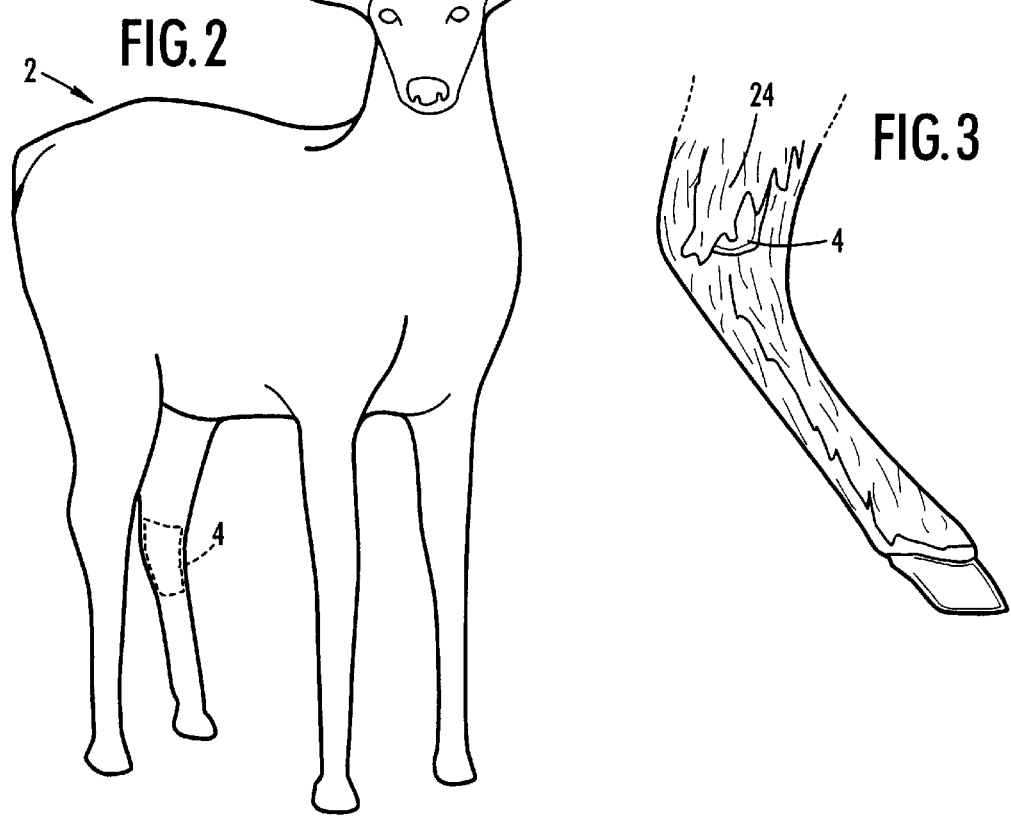
FIG. 3 is a detailed view of the tarsal gland region.

Referring now to the figures, the present invention is an article for attracting deer and a process for making a deer attractant. Deer attractant, generally referred to by reference number 10, comprises an air-permeable container 20 and deer hair 24 held by container 20. In order to create attractant 10, hair 24 from the tarsal gland region 4 of a deer 2 is trimmed so that only hair but no cutaneous tissue, such as hide, gland or muscle, is collected. Although hair 24 from the tarsal gland region 4 is preferred, hair 24 from the preorbital gland region, metatarsal gland region, interdigital gland region, or any other part of the deer may also be used. The region around these glands is defined as the area exposed to the secretions of these glands and which carries those secretions.

Although hair 24 may be collected from a buck, preferably, doe hair is used. Hair 24 is preferably trimmed from a freshly killed deer, but could be cut from a living deer. Electric clippers, scissors, or any other means known in the art for hair cutting may be used for collecting the hair. Preferably nothing is added to the hair to enhance the scent in order to extend the shelf life; however, the application of various attractants to the hair, such as doe urine, buck urine, powdered beaver castor, and acorn oil, is within the scope of the invention.

Next, hair 24 is placed into an air-permeable container 20, that is, a container adapted to allow the scent to emanate. Container 20 preferably has a multiplicity of small holes 22 for air permeability; however, any container that is known in the art for allowing volatile compounds to emanate through it and diffuse into the environment could be used. Container 20 optionally can contain a hook 26 or other means, such as a stake, a strap or an adhesive, to enable container 20 to be attached to an elevated structure or slowly moving vehicle to create a scent trail.

Appropriate packaging or controlled storage environment is not needed for attractant 10 to be useful, but can extend its shelf life by reducing the rate at which volatile compounds volatize. Preferably, attractant 10 is frozen to −20° F. until purchased by a consumer; however, any packaging or other technique known in the art to preserve inorganic compounds—such as an air-impermeable overpack—may be employed to avoid or reduce loss of effectiveness of the hair as an attractant, such U.S. Pat. No. 5,116,649 to Massouda, U.S. Pat. No. 5,122,410 to Löfgren et al., U.S. Pat. No. 5,496,604 to Anderson et al., U.S. Pat. No. 5,508,075 to Roulin et al., U.S. Pat. No. 5,603,974 to Wood, or U.S. Pat. No. 5,725,917 to Parks could be used.

In use, attractant 10 is preferably mounted to an elevated structure, such as a tree. The odor emanating from attractant 10 will entice deer to locate the scent. Between uses, the consumer may place attractant in a freezer or air-impermeable overpack to extend its life.

It will be apparent to those skilled in the art that many changes and substitutions can be made to the preferred embodiment herein described without departing from the spirit and scope of the present invention.

What is claimed is:

1. A deer attractant, comprising:
   hair without cutaneous tissue collected from a region about a gland of a deer; and
   a container carrying said hair.

2. The deer attractant as recited in claim 1, wherein said hair is collected from the tarsal gland region of a deer.

3. The deer attractant as recited in claim 2, wherein said hair is selected from the group consisting of the preorbital gland region, metatarsal gland region, and interdigital gland region.

4. The deer attractant as recited in claim 2, wherein said container has a multiplicity of holes.

5. The deer attractant as recited in claim 2, wherein said container has means for attaching said container to a structure.

6. The deer attractant as recited in claim 2, wherein said hair is from a doe.

7. The deer attractant as recited in claim 1, wherein said hair is selected from the group consisting of the preorbital gland region, metatarsal gland region, and interdigital gland region.

8. The deer attractant as recited in claim 7, wherein said container has a multiplicity of holes.

9. The deer attractant as recited in claim 7, wherein said container has means for attaching said container to a structure.

10. The deer attractant as recited in claim 7, wherein said hair is from a doe.

11. The deer attractant as recited in claim 1, wherein said container has a multiplicity of holes.

12. The deer attractant as recited in claim 11, wherein said container has means for attaching said container to a structure.

13. The deer attractant as recited in claim 1, wherein said container has means for attaching said container to a structure.

14. The deer attractant as recited in claim 13, wherein said attaching means is selected from the group consisting of a hook, a stake, a strap and an adhesive.

15. The deer attractant as recited in claim 1, wherein said hair is from a doe.

16. A deer attractant comprising:
    hair without cutaneous tissue collected from the tarsal gland region of a deer; and
    a container carrying said hair, said container having a plurality of holes.

17. The deer attractant as recited in claim 16, wherein said hair further includes hair selected from the group consisting of the preorbital gland region, metatarsal gland region, and interdigital gland region.

18. The deer attractant as recited in claim 16, wherein said container has means for attaching said container to a structure.

19. The deer attractant as recited in claim 18, wherein said attaching means is selected from the group consisting of a hook, a stake, a strap and an adhesive.

20. The deer attractant as recited in claim 16, wherein said hair is from a doe.

\* \* \* \* \*